(12) United States Patent
Brand et al.

(10) Patent No.: US 6,444,851 B1
(45) Date of Patent: Sep. 3, 2002

(54) PROCESS FOR THE PREPARATION OF MIDODRINE

(75) Inventors: Michael Brand, Raanana; Ronit Chen, Rehovot; Deby Yigal, Tzur Yigal; Joseph Kaspi, Givatayim, all of (IL)

(73) Assignee: Chemagis Ltd., Bnei Brak (IL)

( * ) Notice: Subject to any disclaimer, the term of this patent is extended or adjusted under 35 U.S.C. 154(b) by 0 days.

(21) Appl. No.: 10/040,385

(22) Filed: Jan. 9, 2002

(30) Foreign Application Priority Data

Feb. 26, 2001 (IL) .................................................. 141655

(51) Int. Cl.[7] ...................... C07C 231/12; C07C 233/05
(52) U.S. Cl. ........................ 564/194; 564/196; 564/394
(58) Field of Search ................................ 564/194, 196, 564/394

(56) References Cited

U.S. PATENT DOCUMENTS 3,340,298 A * 9/1967 Karl et al.

FOREIGN PATENT DOCUMENTS

GB           1003659       *   9/1965

* cited by examiner

Primary Examiner—Shailendra Kumar
(74) Attorney, Agent, or Firm—Banner & Witcoff, Ltd.

(57) ABSTRACT

The invention provides a process for the preparation of 2-amino-N-[2-(2,5-dimethoxyphenyl)-2-hydroxyethyl] acetamide of the formula 1 by hydrogenolysis of substituted 2-dibenzylamino-N-[2-(2',5'-dimethoxyphenyl)-2-hydroxy-ethyl]acetamide having the formula (5), wherein Ar and Ar' are aryl groups,

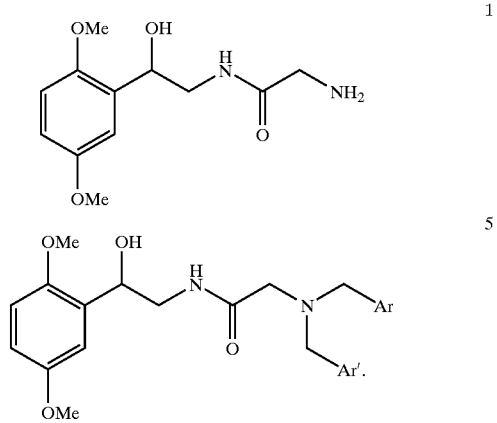

9 Claims, No Drawings

PROCESS FOR THE PREPARATION OF MIDODRINE

This application claims the benefit of and incorporates by reference Israeli application No. 141,655 filed Feb. 26, 2001.

The present invention is related to a novel process for the preparation of 2-amino-N-[2-(2,5-dimethoxyphenyl)-2-hydroxyethyl]acetamide hydrochloride, also known as Midodrine hydrochloride, having the following formula (1).

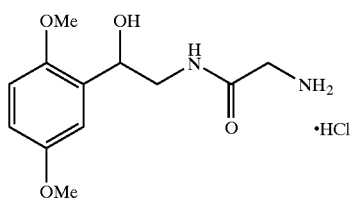

BACKGROUND OF THE INVENTION

Midodrine is classified as an antihypotensive drug. It was first described and claimed in the U.S. Pat. No., 3,340,298. The drug is dispensed in tablet form as the hydrochloride salt having the structure (1).

The key intermediate required for preparing Midodrine is 1-(2,5-dimethoxyphenyl)-2-aminoethanol hydrochloride having the structure (2).

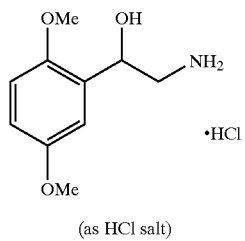

(as HCl salt)

The synthesis of Midodrine HCl consists of reacting the key intermediate (2) with chloroacetyl chloride to afford 2-chloro-N-[2-(2,5-dimethoxyphenyl)-2-hydroxyethyl]acetamide (3). The reaction of (3) with sodium azide will provide 2-azido-N-[2-(2,5-dimethoxyphenyl)-2-hydroxyethyl]acetamide (4) which is subsequently subjected to hydrogenation to afford Midodrine base (6).

Acidification with aqueous HCl will provide Midodrine HCl (1). The above sequence of reactions are outlined in the following scheme (see for example Austrian patent AT 336584).

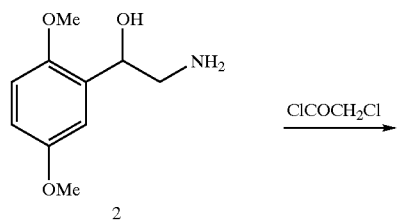

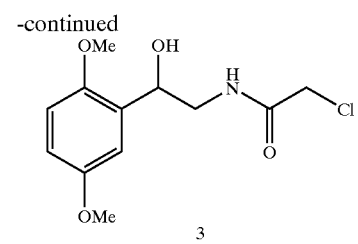

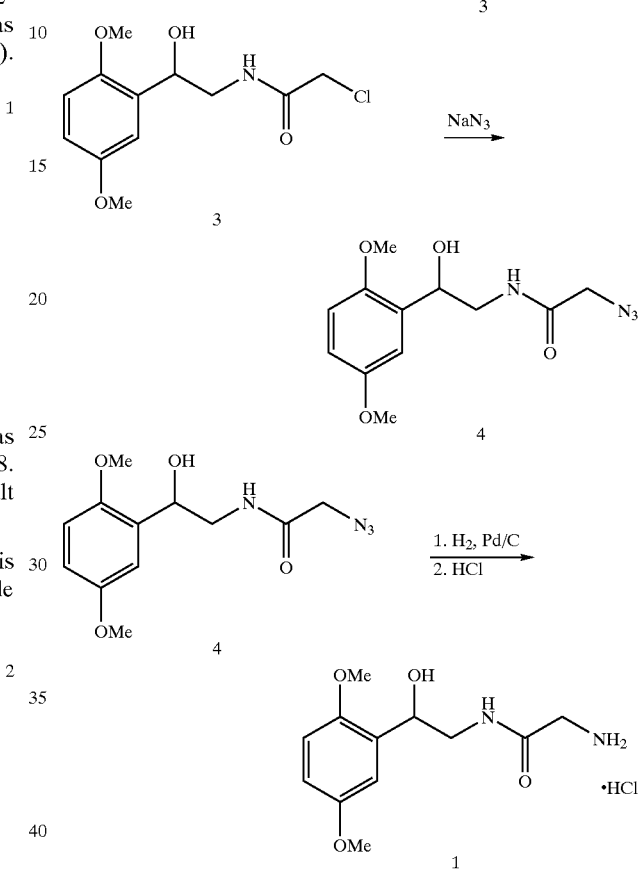

A serious drawback in the above synthesis of Midodrine HCl involves the use of the dangerously explosive sodium azide. In addition, the above synthesis will involve the formation of the organic azide (4), which is also a potentially explosive material. Both sodium azide and the azide (4) are also toxic materials.

The development of a process for Midodrine HCl, which avoids the use of the highly toxic and explosive sodium azide, will be of great benefit.

SUMMARY OF THE INVENTION

According to the present invention, a process is now available for the preparation of Midodrine hydrochloride (1) via a safe process. In addition, all of the intermediates involved in the preparation of (1) are safe to handle. In the present invention, the toxic and potentially explosive sodium azide is replaced by a safe to handle bis (substituted) diaryl amine, preferably dibenzylamine. The new synthesis of Midodrine HCl consists of reacting 1-(2,5-dimethoxyphenyl)-2-aminoethanol hydrochloride (2) with chloroacetyl chloride in a mixture of methylene chloride and aqueous potassium hydroxide solution at 5°–10° C. to produce 2-chloro-N-[2-(2,5-dimethoxyphenyl)-2-hydroxyethyl]-acetamide (3).

The chloro acetamide derivative (3) is not isolated but reacted in situ, after removal of the methylene chloride, with a bis (substituted) diarylamine having formula (6) in refluxing toluene for a period of about 10 hours. Ar and Ar' groups in formula (6) are independently phenyl or substituted phenyl groups.

The substituents can be chosen from $C_1$–$C_4$ alkyl groups, $C_1$–$C_4$ alkoxy groups, $C_1$–$C_4$ dialkylamino groups and halo groups. The preferred amine of formula (6) is dibenzyl amine of formula (8) wherein both Ar and Ar' groups are phenyl groups The product, 2-(substituted)-dibenzylamino-N-[2-(2,5-dimethoxyphenyl)-2-hydroxyethyl]acetamide (5) is isolated by filtration. In the next step, the intermediate (5) is hydrogenolyzed to give Midodrine free base (9). The hydrogenolysis is performed at 40°–70° C., preferably 50° C., and 4–6 bar hydrogen pressure using 5% Pd/C as catalyst. The reaction is performed in an alcoholic medium, preferably ethanol. After removal of the alcohol, the Midodrine base (9) is isolated by filtration.

In the final step, the Midodrine base (9) is dissolved in ethanol. The addition of a solution of HCl gas in isopropanol causes the hydrochloride salt of Midodrine to separate from solution. A filtration will afford Midodrine HCl (1) in a highly pure form.

It should be pointed out that all of the reagents as well as the intermediates involved in the process can be safely handled and provide no safety risks. The above sequence of reactions is outlined in the following scheme.

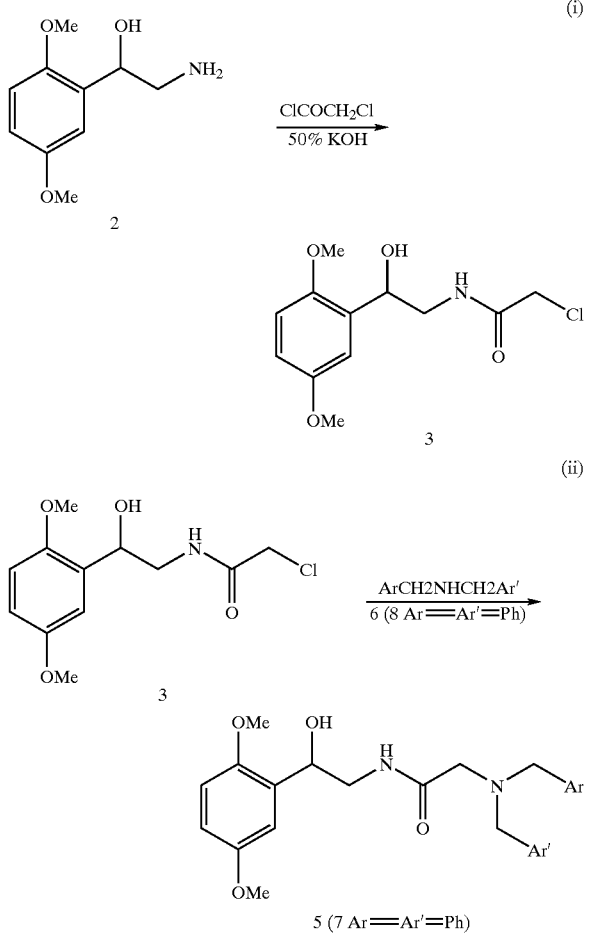

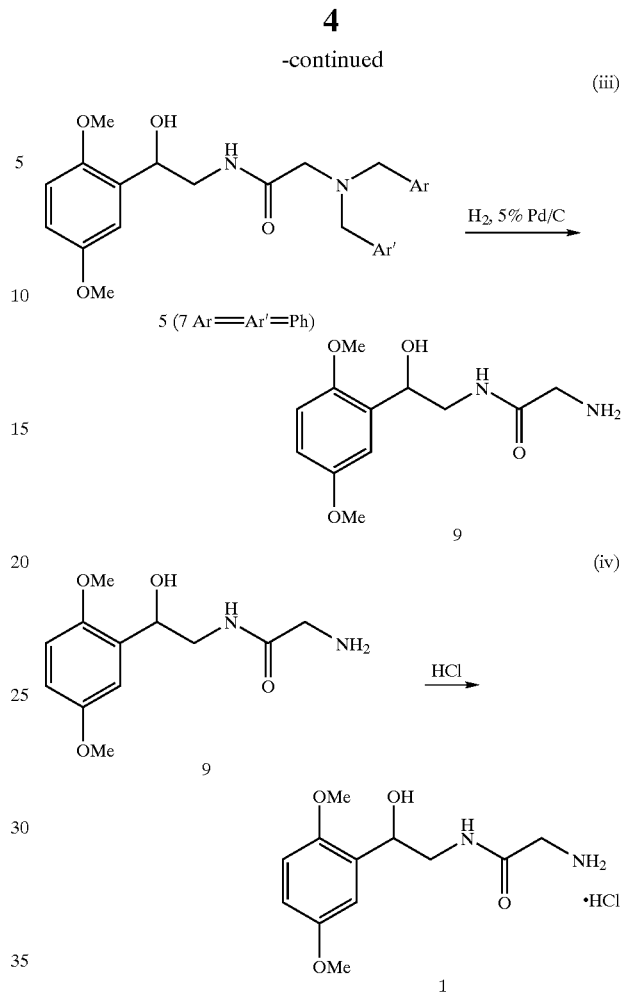

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

Preparation of 2-chloro-N-[2-(2,5-dimethoxyphenyl)-2-hydroxyethyl]acetamide

The reaction vessel is charged with 15.5 g 1-(2,5-dimethoxyphenyl)-2-amino-ethanol hydrochloride, 115 ml methylene chloride and 100 ml water. The mixture is stirred at 25°–30° C. to afford a clear two-phase mixture. The mixture is cooled to 5°–10° C. and a solution of 18.7 g of 50% potassium hydroxide and 18.5 ml water is added in portions at 50°–10° C.

The mixture is stirred at 5°–10° C. for 15 min. 8.0 ml of chloroacetyl chloride is added in portions at 5°–10° C. causing an exothermic reaction to occur. On completion of the addition, the pH should be adjusted to 3–6. The mixture is allowed to warm to 25°–30° C. and the pH is adjusted again to 3–6. After stirring for one hour at 25°–30° C., the pH is adjusted to 6–7 with 5% aqueous potassium hydroxide solution. The stirring is stopped and the layers are separated.

The upper aqueous layer is washed with 25 ml of methylene chloride. The organic layers are combined and dried over magnesium sulfate. The solution of 2-chloro-N-[2-(2,5-dimethoxyphenyl)-2-hydroxyethyl]acetamide in methylene chloride is used as is in the next step.

Example 2

Preparation of 2-dibenzylamino-N-[2-(2,5-dimethoxyphenyl)-2-hydroxyethyl]acetamide The reaction vessel is charged with the methylene chloride solution of 2-chloro-N-[2-(2,5-dimethoxyphenyl)-2-hydroxyethyl]acetamide prepared in example 1. The majority of the methylene chloride is distilled off at atmospheric pressure. On completion of the distillation 155 ml toluene are added. The mixture is stirred to obtain a solution. 45 to 50 ml of the toluene is distilled to remove the remainder of methylene chloride. The mixture is cooled to 85°–90° C. and 28.4 g dibenzylamine is added in portions at 85°–90° C. On completion of the addition, the mixture is heated to reflux for a period of 10 hours.

On completion of reaction, the resulting suspension is cooled to 45°–50° C. 110 ml water are added followed by 7.5 g of 50% potassium hydroxide. The mixture is stirred at 25°–30° C. for a period of 2–3 hours during which time the product crystallizes from solution. After cooling to 5°–10° C., the product is filtered to afford 21.7 g of 2-dibenzylamino-N-[2-(2,5-dimethoxyphenyl)-2-hydroxyethyl]acetamide. This represents a 75% yield based on the starting material from example 1. The product is characterized as follows:

m.p.: 110.0–111.1° C.

MS: 434 (M+)

$^1$H-NMR (DMSO-$d_6$): 7.65 ppm, triplet, J=6 Hz, CH$_2$—NH, 1H; 7.35–7.26 ppm, multiplet, benzyl aromatic protons, 10H; 7.06–6.81 ppm, multiplet, dimethoxy aromatic protons, 3H; 5.60 ppm, doublet, J=5 Hz, CH—OH, 1H; 4.95 ppm, multiplet, CH—OH, 1H; 3.71 and 3.65 ppm, two singlets, two OCH$_3$, 6H; 3.54 ppm, broad singlet, two CH$_2$—Ph, 4H; 3.36 ppm, singlet, H$_2$O; 3.45 and 3.15 ppm, two multiplets, CH$_2$—NH, 2H; 2.93 ppm, broad singlet, CH$_2$—N, 2H.

$^{13}$C-NMR (DMSO-$d_6$): 169.62 ppm, $C_{11}$; 153.19+149.82 ppm, $C_1$+$C_4$; 138.21 ppm, $C_{15}$/$C_{21}$; 132.26 ppm, $C_6$; 128.78 ppm, $C_{16}$/$C_{20}$/$C_{22}$/$C_{26}$; 128.31 ppm, $C_{17}$/$C_{19}$/$C_{23}$/$C_{25}$; 127.14 ppm, $C_{18}$/$C_{24}$; 112.79+112.25+111.59 ppm, $C_2$+$C_3$+$C_5$; 65.49 ppm, $C_9$; 57.72 ppm, $C_{13}$/$C_{14}$; 56.45 ppm, $C_{12}$; 55.80+55.18 ppm, $C_7$+$C_8$; 44.38 ppm, $C_{10}$.

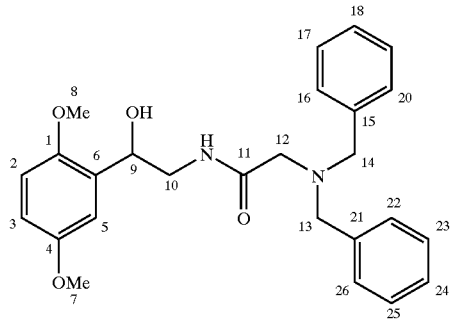

Example 3

Preparation of 2-amino-N-[2-(2,5-dimethoxyphenyl)-2-hydroxyethyl]acetamide (Midodrine base)

An autoclave is charged with 15.0 g of 2-dibenzylamino-N-[2-(2,5-dimethoxyphenyl)-2-hydroxyethyl]acetamide, 200 ml ethanol and 1.5 g of 5% Pd/C catalyst. The system is flushed three times with nitrogen followed by hydrogen. The pressure of hydrogen is adjusted to 4–6 bar. The temperature is adjusted to 45°–50° C. The mixture is stirred and heated at 45°–50° C. for 24 hours.

On reaction completion, the mixture is cooled to 25°–30° C. and filtered through a Celite pad to separate the catalyst. The clear filtrate is transferred to a clean reaction vessel. About ½ of the ethanol is distilled out at atmospheric pressure. On cooling and seeding, Midodrine base will crystallize from solution. After cooling to 5°–10° C., the product is filtered to afford 6.3 g (71% yield) of white Midodrine base. The product is characterized as follows:

m.p.: 105.8°–106.8° C.

MS: 254 (M+)

$^1$H-NMR (DMSO-$d_6$): 7.88 ppm, triplet, J=6 HZ, CH$_2$—NH, 1H 7.02–6.76 ppm, multiplet, aromatic protons, 3H; 5.42 ppm: broad singlet, CH—OH, 1H; 4.90 ppm, multiplet, CH—OH, 1H; 3.73+3.70 ppm, two singlets, two OCH$_3$, 6H; 3.45+3.01 ppm, two multiplets, CH$_2$—NH, 2H, 3.06 ppm, broad singlet, CH$_2$—NH$_2$, 2H.

$^{13}$C-NMR(DMSO-$d_6$): 172.75 ppm, $C_{11}$; 153.11+149.65 ppm, $C_1$+$C_4$; 132.45 ppm, $C_6$; 112.53+112.17+111.48 ppm, $C_2$+$C_3$+$C_5$; 65.64 ppm, $C_9$; 55.74+55.18 ppm, $C_7$+$C_8$; 44.82+44.54 ppm, $C_{10}$+$C_{12}$.

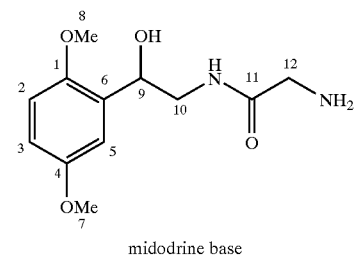

midodrine base

Example 4

Conversion of Midodrine Base to Midodrine Hydrochloride

The reaction vessel is charged with 5.0 g Midodrine base and 60 ml ethanol. The mixture is heated to reflux to obtain a clear solution. To the hot mixture is added 6.3 ml of a 22% solution of hydrochloric acid in isopropanol in portions. During the addition, the Midodrine HCl will crystallize from solution. After cooling to 5°–10° C., the product is filtered to afford 4.8 g (96% yield) of Midodrine HCl (m.p.: 200.8°–201.8° C.).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the preparation of 2-amino-N-[2-(2,5-dimethoxyphenyl)-2-hydroxyethyl]acetamide HCl of the formula 1 by hydrogenolysis of substituted 2-dibenzylamino-N-[2-(2',5'-dimethoxyphenyl)-2-hydroxyethyl]acetamide having the formula (5), wherein Ar and Ar' are aryl groups,

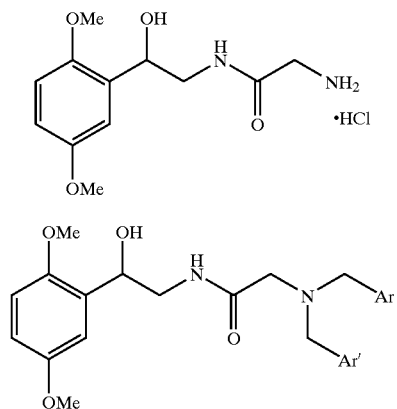

2. A process according to claim 1 in which the compound of formula (5) is prepared by reacting 2-chloro-N-[2-(2,5-dimethoxyphenyl)-2-hydroxy-ethyl]acetamide of formula (3) with a substituted dibenzylamine of the formula (6):

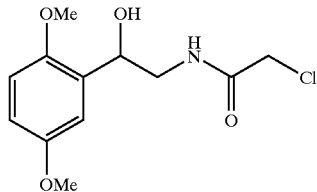

ArCH$_2$NHCH$_2$Ar'  6 wherein Ar and Ar' are optionally substituted phenyl groups.

3. A process according to claim 2 wherein the ary Ar and Ar' groups are independently phenyl or substituted phenyl groups wherein these substituents are chosen from $C_1$–$C_4$ alkyl groups, $C_1$–$C_4$ alkoxy groups, $C_1$–$C_4$ dialkylamino groups and halo groups.

4. A process according to claim 3 wherein both Ar and Ar' groups in formula (6) are phenyl groups.

5. A process according to claim 1 wherein the hydrogenolysis reaction is done by hydrogen over a palladium on carbon catalyst.

6. A process according to claim 3 wherein the hydrogen pressure is between 4–6 bars.

7. A process according to claim 3 or 4 wherein the reaction temperature is between 40°–70° C.

8. A process according to claim 3, 4, or 5 wherein the reaction medium is an alcohol of the formula ROH in which R is a $C_1$–$C_4$ alkyl group.

9. A process according to claim 6 wherein the reaction medium is ethanol.

* * * * *

UNITED STATES PATENT AND TRADEMARK OFFICE
CERTIFICATE OF CORRECTION

PATENT NO.    : 6,444,851 B1
DATED         : September 3, 2002
INVENTOR(S)   : Michael Brand et al.

It is certified that error appears in the above-identified patent and that said Letters Patent is hereby corrected as shown below:

Column 8,
Line 22, "ary" has been replaced with -- aryl --,
Line 37, "or" has been replaced with -- and --.

Signed and Sealed this

Eighteenth Day of March, 2003

JAMES E. ROGAN
*Director of the United States Patent and Trademark Office*